(12) United States Patent
Harks et al.

(10) Patent No.: US 11,000,336 B2
(45) Date of Patent: May 11, 2021

(54) VISUALIZATION OF AN IMAGE OBJECT RELATING TO AN INSTRUCMENT IN AN EXTRACORPOREAL IMAGE

(71) Applicant: KONINKLIJKE PHILIPS N.V., Eindhoven (NL)

(72) Inventors: Godefridus Antonius Harks, Rijen (NL); Niels Nijhof, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 101 days.

(21) Appl. No.: 16/335,002

(22) PCT Filed: Sep. 18, 2017

(86) PCT No.: PCT/EP2017/073379
§ 371 (c)(1),
(2) Date: Mar. 20, 2019

(87) PCT Pub. No.: WO2018/054796
PCT Pub. Date: Mar. 29, 2018

(65) Prior Publication Data
US 2019/0247132 A1 Aug. 15, 2019

(30) Foreign Application Priority Data
Sep. 23, 2016 (EP) ..................... 16190267

(51) Int. Cl.
*A61B 34/00* (2016.01)
*A61B 8/08* (2006.01)
(Continued)

(52) U.S. Cl.
CPC ............. *A61B 34/25* (2016.02); *A61B 6/12* (2013.01); *A61B 6/5247* (2013.01);
(Continued)

(58) Field of Classification Search
CPC ....... A61B 34/20; A61B 34/25; A61B 5/0084; A61B 6/12; A61B 6/5247; A61B 6/5288;
(Continued)

(56) References Cited

U.S. PATENT DOCUMENTS 6,016,439 A * 1/2000 Acker ............... A61B 5/06 600/411
6,470,207 B1 * 10/2002 Simon ............... G16H 40/63 600/426

(Continued)

FOREIGN PATENT DOCUMENTS

EP 1504713 A1 2/2005
WO 2011070477 A1 6/2011
(Continued)

*Primary Examiner* — Michelle M Entezari

(57) ABSTRACT

The invention relates to an apparatus and a system for visualizing an image object relating to an instrument (3), particularly a medical instrument, in an extracorporeal image. The image object may comprise a representation of the instrument (3) or an intracorporeal image (40) acquired using the instrument (3). The system comprises an extracorporeal image acquisition device (1) for acquiring extracorporeal images with respect to an extracorporeal image frame and a tracking arrangement (2) for tracking the instrument (3) independent of the extracorporeal images with respect to a tracking frame. Further, the invention relates to a method carried out in the system.

20 Claims, 5 Drawing Sheets

(51) Int. Cl.
  *A61B 6/00* (2006.01)
  *A61B 6/12* (2006.01)
  *A61B 8/00* (2006.01)
  *A61B 34/20* (2016.01)
  *A61B 5/00* (2006.01)
  *G06T 7/30* (2017.01)
  *G06T 7/70* (2017.01)
  *G06T 7/20* (2017.01)

(52) U.S. Cl.
  CPC ............ *A61B 6/5288* (2013.01); *A61B 8/461* (2013.01); *A61B 8/5284* (2013.01); *A61B 34/20* (2016.02); *G06T 7/20* (2013.01); *G06T 7/30* (2017.01); *G06T 7/70* (2017.01); *A61B 5/0084* (2013.01); *A61B 2034/2051* (2016.02); *A61B 2034/2055* (2016.02); *A61B 2034/2063* (2016.02); *A61B 2034/2065* (2016.02); *A61B 2034/2074* (2016.02); *G06T 2207/10101* (2013.01); *G06T 2207/10116* (2013.01); *G06T 2207/10132* (2013.01)

(58) Field of Classification Search
  CPC ......... A61B 8/461; A61B 8/5284; G06T 7/20; G06T 2207/10101; G06T 2207/10116; G06T 2207/10132; G06T 7/30; G06T 7/70
  See application file for complete search history.

(56) References Cited

U.S. PATENT DOCUMENTS

| | | | |
|---|---|---|---|
| 7,824,328 B2 * | 11/2010 | Gattani | A61B 34/20 600/117 |
| 8,849,374 B2 * | 9/2014 | Yamamoto | A61B 34/20 600/424 |
| 9,119,552 B2 * | 9/2015 | Baumann | A61B 5/065 |
| 9,519,341 B2 * | 12/2016 | Hasegawa | A61B 34/74 |
| 9,662,042 B2 * | 5/2017 | Akimoto | A61B 1/00009 |
| 10,085,705 B2 * | 10/2018 | Nakagawa | G06T 7/251 |
| 10,335,237 B2 * | 7/2019 | Christian | A61B 34/10 |
| 2002/0044631 A1 * | 4/2002 | Graumann | A61B 6/547 378/205 |
| 2003/0130576 A1 | 7/2003 | Seeley | |
| 2005/0055174 A1 * | 3/2005 | David | A61B 34/20 702/152 |
| 2006/0025677 A1 * | 2/2006 | Verard | A61B 34/20 600/423 |
| 2008/0200927 A1 * | 8/2008 | Hartmann | A61B 90/36 606/130 |
| 2008/0242978 A1 * | 10/2008 | Simon | A61B 90/36 600/426 |
| 2008/0300478 A1 | 12/2008 | Zuhars | |
| 2009/0234444 A1 * | 9/2009 | Maschke | A61B 5/411 623/2.11 |
| 2009/0253978 A1 * | 10/2009 | Hashimshony | G06F 19/00 600/407 |
| 2010/0030063 A1 * | 2/2010 | Lee | A61B 5/065 600/424 |
| 2010/0234724 A1 * | 9/2010 | Jacobsen | A61B 90/37 600/424 |
| 2011/0268325 A1 * | 11/2011 | Teichman | G06T 19/006 382/128 |
| 2012/0245458 A1 | 9/2012 | Gogin | |
| 2013/0169624 A1 * | 7/2013 | Bourier | A61B 34/10 345/419 |
| 2014/0193336 A1 * | 7/2014 | Rousso | A61B 6/503 424/1.65 |
| 2015/0250434 A1 | 9/2015 | Hall | |
| 2015/0320514 A1 * | 11/2015 | Ahn | A61B 34/30 606/130 |
| 2018/0101950 A1 * | 4/2018 | Gliner | G06T 7/0012 |
| 2020/0337784 A1 * | 10/2020 | Krebs | A61B 17/1703 |

FOREIGN PATENT DOCUMENTS

| | | |
|---|---|---|
| WO | 2012143885 A2 | 10/2012 |
| WO | 2013136247 A1 | 9/2013 |

* cited by examiner

VISUALIZATION OF AN IMAGE OBJECT RELATING TO AN INSTRUCMENT IN AN EXTRACORPOREAL IMAGE

CROSS-REFERENCE TO PRIOR APPLICATIONS

This application is the U.S. National Phase application under 35 U.S.C. § 371 of International Application No. PCT/EP2017/073379, filed on Sep. 18, 2017, which claims the benefit of European Patent Application No. 16190267.1, filed on Sep. 23, 2016. These applications are hereby incorporated by reference herein.

FIELD OF THE INVENTION

The invention relates to an apparatus, a system and a method for visualization of an image object relating to an instrument in an extracorporeal image. Moreover, the invention relates to a computer program for carrying out the method using a processing unit.

BACKGROUND OF THE INVENTION

In medical interventions, fluoroscopy is often employed in order to track the position and orientation of instruments inserted into a region of interest within a body of a patient. In fluoroscopy, x-ray images of the region of interest are (quasi-) continuously acquired so that moving x-ray images are generated which allow a physician to track the instruments substantially in real time in relation to surrounding body structures in the region of interest.

Moreover, fluoroscopy is sometimes used in connection with other imaging modalities, such as ultrasound imaging. The additional ultrasound images particularly allow seeing soft tissue in the region of interest, which is barely visible in the fluoroscopic x-ray images. In this regard, WO 2011/070477 discloses a system in which ultrasound images are fused with fluoroscopic x-ray images so that the x-ray images are overlaid with the ultrasound images. In order to appropriately arrange the ultrasound images relative to the x-ray images, the system tracks the position and orientation of the ultrasound probe in the fluoroscopic images and fuses the x-ray images and the ultrasound images on the basis of the detected position and orientation of the ultrasound probe.

EP 1504713 A1 discloses an image guided navigation system, wherein an x-ray imaging device generates images of the region of a patient, a tracking device tracks the location of the instrument in a region of the patient, a controller superimposes an icon representative of the instrument onto the images generated from the imaging device based upon the location of the instrument. Patient registration, determining how to correlate the position of the instrument on the patient to the position on the diagnostic or pre-acquired images, is performed by the physician or user selecting and storing particular points from the pre-acquired images and then touching the corresponding points on the patient's anatomy with a pointer probe. The navigation system analyzes the relationship between the two sets of points that are selected and computes a match, which correlates every point in the image data with its corresponding point on the patient's anatomy or the patient space. The points that are selected to perform registration are the fiducial arrays or landmarks identifiable on the images and identifiable and accessible on the patient, wherein the landmarks can be artificial landmarks that are positioned on the patient or anatomical landmarks (e.g. vertebrae, vessels) that can be easily identified in the image data.

US 2003/0130576 A1 discloses a fluoroscopic tracking and visualization system that employs a tracker and a set of substantially non-shadowing point markers, arranged in a fixed pattern or set in a fluoroscope calibration fixture that is imaged in each shot. The fixture is preferably affixed to the image detector of the fluoroscope, and tracking elements employing magnetic field and being secured with respect to the fixture and at least one of a tool and the patient, provide respective position data irrespective of movement. A marker detection module identifies markers imaged in each shot, and a processor applies the known marker positions to model the projection geometry, e.g., camera axis and focus, for the shot and, together with the tracked tool position, form a corrected tool navigation image.

US 2008/0300478 A1 discloses an electromagnetic surgical navigation system comprising a fluoroscopic imaging apparatus, wherein at least one tracking element acts as a navigation reference that is attached to patient or table near patient in the surgical field of interest. The navigation reference creates a navigation reference frame for the surgical navigation system around the patient's anatomy in the surgical field of interest. The navigation reference used by the surgical navigation system is registered to the patient's anatomy prior to performing image-guided surgery or surgical navigation. The registration is defined by identifying a common set of coordinate registration points on the various images that may be tracked using a tracking system. Instead of using fiducials, tracking systems may employ an initialization process wherein the surgeon touches a number of points on a patient's anatomy in order to define an external coordinate system in relation to the patient's anatomy and to initiate tracking. The surgical navigation system uses a gating signal associated with an ongoing body activity to determine which image in a sequence of acquired images best represents the state of the imaged anatomy at a given point in time and displays navigated surgical instruments within that image at that point in time.

In applications of the aforementioned types, fluoroscopic x-ray images are (quasi-) continuously acquired in order to visualize changing objects—e.g. moving instruments or changing ultrasound images—in real-time. This also means that the patient and staff are continuously exposed to ionizing x-ray radiation in these applications. This may have a detrimental effect on the health of the patient and staff.

SUMMARY OF THE INVENTION

It is an object of the present invention to provide intuitive visualization of changing objects in extracorporeal images of a region of interest of a body.

According to a first aspect of the invention an apparatus is provided for visualizing an image object relating to an instrument in an extracorporeal image, wherein the apparatus is configured to:

receive at least one extracorporeal image of a region of interest comprising a projection of the instrument onto an imaging plane with respect to an extracorporeal image frame from an extracorporeal image acquisition system;

determine a position and/or orientation of the instrument in the extracorporeal image frame by matching a projection of a graphical model of the instrument to the projection of the instrument onto the imaging plane;

receive temporal information on positions and/or orientations of the instrument in the region of interest with respect to a tracking frame from a tracking arrangement;

register the position and/or orientation of the instrument in the extracorporeal image frame to the position and/or orientation of the instrument in the region of interest with respect to a tracking frame in an initial instance;

transform the positions and/or orientations of the instrument from the tracking frame at any later instance into the extracorporeal image frame using a transform;

output a visualization of the image object in the at least one extracorporeal image based on the transform, wherein the image object relates to a position and/or an orientation of the instrument at a later instance than when the at least one extracorporeal image is acquired.

The invention provides an intuitive visualization of an actualized position and/or orientation of an instrument on a previously acquired extracorporeal image, without needing an actualization of the extracorporeal image. The extracorporeal image may be one of a fluoroscopy image, a magnetic resonance image, an ultrasound image and a computed tomography image.

In an embodiment, the apparatus is further configured to:
receive an intracorporeal image from an imaging probe of the instrument,
and wherein the image object corresponds to the intracorporeal image acquired using the imaging probe. It is an advantage of the embodiment that a higher resolution intracorporeal image is provided for a specific location related to the position and/or orientation of the instrument within the region of interest, wherein the region of interest is represented at a lower resolution in the extracorporeal image.

In a further embodiment, the visualization comprises overlaying the image object over the extracorporeal image and the apparatus is configured to arrange the image object relative to the extracorporeal image in accordance with the position and/or orientation of the imaging probe in the extracorporeal image frame. It is an advantage of the embodiment to provide the image object at the actual position and orientation of the instrument with respect to the extracorporeal image, as the user is able to navigate the instrument within the region of interest in the body by using an older extracorporeal image, and thereby not spending time on actualizing the extracorporeal image for confirming the projection of the instrument in the extracorporeal image.

In yet another embodiment, the intracorporeal image is one of an ultrasound image and an optical coherence tomography image. It is an advantage of the embodiment to provide a high resolution intracorporeal image of a specific location within the region of interest, on which the user can base diagnostic or treatment decisions related to the anatomy visualized at lower resolution on the extracorporeal image.

In an embodiment, the image object comprises a representation of the instrument, wherein the representation of the instrument comprises a mark representing one of a predetermined point of the instrument, a projection of a model of the instrument and an expanded graphical model of the instrument. It is a benefit of the embodiment that the user can follow position change of a portion of the instrument without being distracted by too many details regarding the projection of the instrument in the extracorporeal image.

In a second aspect of the invention a system is provided, comprising the apparatus according to the invention, the extracorporeal image acquisition system, the tracking arrangement and the instrument.

In an embodiment of the system the extracorporeal image acquisition system is based on x-ray. It is an advantage of the embodiment that it allows intuitive navigation of an instrument in the most accepted clinical setting. The exposure to x-ray radiation of the patient and the physician is reduced by the visualization of the actual position of the instrument on an older x-ray image.

In another embodiment of the system, the extracorporeal image is selected from a plurality of stored x-ray images of the region of interest acquired for different phases of a motion of the region of interest, the selected image being acquired for a phase of the motion of the region of interest occurring when the position and/or orientation of the instrument is determined using the tracking arrangement. It is an advantage of the embodiment to discriminate in the visualization between changes of position and/or orientation of the instrument originating from cyclical motion (inherent motion caused by heart motion, breathing) and changes of position and/or orientation of the instrument upon an action of the user, such as navigation through vessels for targeting diagnostic or treatment of a location within the region of interest.

In a further embodiment, the system comprises a monitoring device configured to acquire at least one measurement signal indicative of the phase of the motion of the region of interest, wherein the apparatus is configured to identify the phase of the motion of the region of interest occurring when the changed position and/or orientation of the instrument is determined on the basis of the measurement signal. It is an advantage of the embodiment to associate the changes of position and/or orientation of the instrument due to the inherent motion within the region of interest to a signal that provides information on the phase of the cyclical motion.

According to a third aspect, the invention provides a method of visualizing an image object relating to an instrument in an extracorporeal image, comprising:

receiving at least one extracorporeal image of a region of interest comprising a projection of the instrument onto an imaging plane with respect to an extracorporeal image frame;

determining a position and/or orientation of the instrument in the extracorporeal image frame by matching a projection of a graphical model of the instrument to the projection of the instrument onto the imaging plane receiving temporal information on positions and/or orientations of the instrument in the region of interest with respect to a tracking frame;

registering the position and/or orientation of the instrument in the extracorporeal image frame to the position and/or orientation of the instrument in the region of interest with respect to a tracking frame in an initial instance;

transforming the positions and/or orientations of the instrument from the tracking frame at any later instance into the extracorporeal image frame by using a transform;

outputting a visualization of the image object in the at least one extracorporeal image based on the transform, wherein the image object relates to a position and/or an orientation of the instrument at a later instance than when the at least one extracorporeal image is acquired.

It shall be understood that an embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
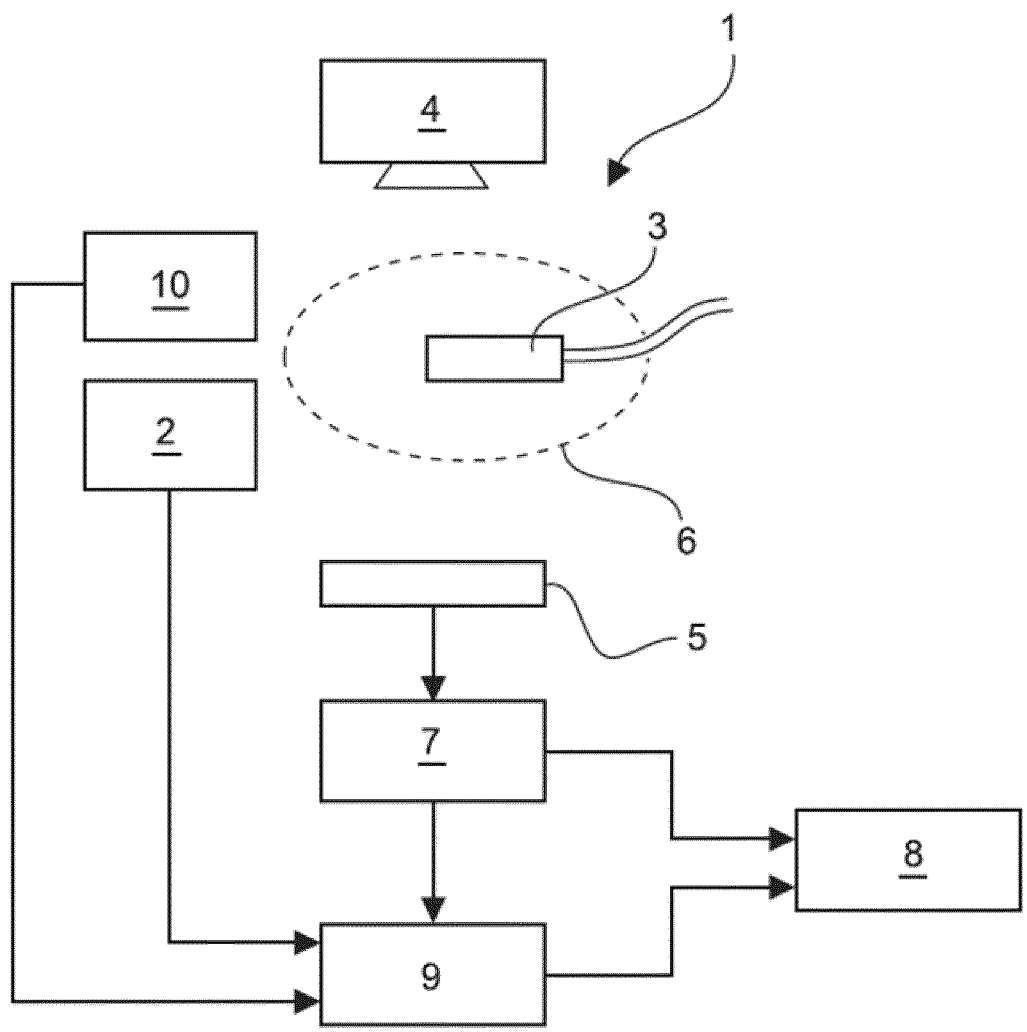
FIG. 1 schematically and exemplarily shows components of a first embodiment of a system according to the invention.

FIG. 1 schematically and exemplarily shows a first embodiment of a system comprising an extracorporeal image acquisition system 1 used in order to provide images of a region of interest within a human or animal patient body for diagnostic purposes and/or during surgical interventions (particularly minimally invasive surgical interventions). The region of interest may include the heart of the patient as it is the case in one embodiment referred to herein below. However, the system may likewise be used in order to image other body regions.

The extracorporeal image acquisition system 1 may be one of an x-ray based imaging device, a magnetic resonance imaging device or an ultrasound imaging system, capable of providing images of the interior of the body of the patient.

In the following, for elucidating the invention, the x-ray device is used as extracorporeal image acquisition system, however it can be understood by those skilled in the art that an x-ray image of a body region can be substituted by a magnetic resonance image or by an ultrasound image of the body region, in order to practice the invention.

The system in FIG. 1 further comprises a tracking arrangement 2 configured to track the position and/or orientation of an instrument 3, particularly a medical instrument, used in the region of interest. The instruments 3 the position and/or orientation of which can be tracked in the imaging system include any instruments 3 which have sufficiently high x-ray attenuation coefficients in order for them to be visible in the x-ray images. Examples of such instruments 3 include instruments for minimally invasive surgical interventions, such as, for example, catheters, sheaths, needles and guide wires, which are made of a material having suitable x-ray attenuation properties. Further examples, which will also be referred again herein below, include imaging probes, such as ultrasound probes, endoscopes and optical coherence tomography (OCT) catheters, which are guided to specific locations within the region of interest imaged by the x-ray device 1 in order to obtain further image information in addition to x-ray images.

The x-ray device 1 particularly comprises an x-ray source 4 and an x-ray detector 5 which faces the x-ray source 4. The x-ray source 4 is configured to emit x-ray radiation which traverses an examination region 6 arranged between the x-ray source 4 and the x-ray detector 5. For generating the x-ray radiation, the x-ray source 4 may particularly comprise an x-ray tube. The x-ray detector 5 is configured to acquire projection values of objects in the examination region 6, which correspond to the x-ray radiation intensity arriving at the radiation detector 5 upon attenuation by the objects. It may include a digital radiation detector comprising a two-dimensional array of detector elements, where each detector element corresponds to a pixel of the generated x-ray images. The projection values acquired by the x-ray detector 5 are provided to an image generation unit 7 which generates two-dimensional electronic images on the basis of the projection values. These images can particularly be displayed on a display unit 8, which may comprise one or more monitor screens.

In use of the imaging system, the region of interest of the patient body (not shown in the figures) is positioned in the examination region 6 on a suitable support, such as a patient table, so that the region of interest can be imaged under a certain angle. Further, the x-ray source 4 and the x-ray detector 5 may optionally be mounted on a gantry, such as a C-arm gantry, which allows for rotating the x-ray source 4 and x-ray detector 6 synchronously around the examination region 6. This allows for imaging the region of interest under different angles.

The x-ray device 1 is configured as a fluoroscopy device. This means that the x-ray device 1 is configured quasi-continuously obtain x-ray images in short time intervals so that moving x-ray images of the region of the interest and the instrument 3 used therein can be generated. When the tracking arrangement 2 is applied to track the position and/or orientation of the instrument 3, no x-ray images are acquired. In that far, it is not necessary that the x-ray device 1 is capable of generating fluoroscopic x-ray images in order to allow for a tracking of the motion of the instrument 3. However, the tracking arrangement 2 may only temporarily be employed in the imaging system and fluoroscopic moving images may be acquired in order to allow for tracking the motion of the instrument 3, when the tracking arrangement 2 is not used. Moreover, as will be explained in more detail herein below, the x-ray device 1 may be controlled to acquire moving images of one or more periods of a periodic motion of the region of interest, such as respiratory motion and/or heart motion, prior to the tracking of the instrument 3 by means of the tracking arrangement 2. These images may be stored and used for visualizing the position and/or orientation of the instrument 3, when it is tracked using the tracking arrangement 2.

In one embodiment, the tracking arrangement 2 is configured to track the position of points of the instrument 3. In this case, the orientation of the object is indicated by the relative arrangement of the points to each other and may not be directly measured. In further embodiments, the tracking arrangement 2 is configured to directly track the orientation of the instrument 3 in addition to the position(s) of one or more point(s) of the instrument 3. For this purpose, the tracking arrangement 2 may comprise an orientation-sensitive sensor, such as, for example, a magnetic field sensor.

In order to implement these embodiments, any suitable tracking technique may be used which is known to the person skilled in the art. Only by way of example, some suitable tracking techniques and corresponding configurations of the tracking arrangement 2 are explained in the following.

In accordance with one example, electromagnetic tracking may be applied. In one implementation of this example, the tracking arrangement 2 comprises a field generator arranged which is configured to generate an inhomogeneous magnetic field with a known geometry in the tracking region (i.e. the region in which the position and/or orientation of the instrument 3 can be tracked). Moreover, the instrument 3 is equipped with one or more magnetic field sensor(s) for measuring the magnetic field, and the tracking arrangement 2 further comprises an evaluation unit coupled to the magnetic field sensor(s), e.g. through a wired connection. The sensor signals are transmitted to the evaluation unit and the evaluation unit determines the position(s) and/or orientations of the magnetic field sensor(s)—and, thus, of the instrument 3—from the sensor signals on the basis of the known geometry of the magnetic field.

In a further implementation of this example, the instrument 3 is equipped with one or more magnet(s), which may particularly be permanent magnets, and the tracking arrangement 2 comprises magnetic field sensor for measuring the magnetic field generated by these one or more magnet(s) outside the patient body. On the basis of the magnetic field measurements, the tracking arrangement 2 determines the position(s) and/or orientation(s) of the magnet(s) and, thus, the instrument 3.

In a further example, the tracking arrangement 2 comprises an impedance-based tracking system. In this example, the tracking arrangement 2 comprises a plurality of electrodes placed on the surface of the patient body. Further electrodes are arranged on the instrument 3, and electric currents are driven between these electrodes and the electrodes placed on the body surface. The tracking arrangement 2 measures the impedance between the electrodes of the instrument 3 and each of the body surface electrodes and determines the positions of the electrodes of the instrument 3 on the basis of these impedance measurements. A corresponding exemplary impedance-based tracking system is described in U.S. Pat. No. 7,756,576, for example.

As a further alternative, the tracking arrangement 2 uses optical shape sensing for tracking the position and orientation of the instrument 3. In this case, the instrument 3 comprises a tube or is attached to the distal end of a tube which is affixed to a known reference point in space. Into the tube, an optical shape sensing fiber is integrated which may extend along the longitudinal extension of the tube, and the tracking arrangement 2 comprises an optical shape sensing device which is configured to determine the shape of the shape sensing fiber. For this purpose, the shape sensing fiber may be provided with strain-sensitive sensors, and the optical shape sensing device may inject light into the shape sensing fiber and determine the shape of the optical shape sensing fiber from light reflected by the sensors. One example of a suitable technique for determining the shape of the optical fiber in such a way is disclosed in WO 2013/136247. On the basis of the determined shape and the known position of the reference point, the tracking arrangement 2 can then determine that position and/or orientation of the instrument 3.

Moreover, in accordance with a further example, the tracking arrangement 2 may determine the position and/or orientation of the instrument 3 by means of a navigation satellite system. In this example, the instrument 3 may be equipped with receivers for receiving the signals of the navigation satellites. On the basis of these signals the positions of the receivers may be determined in a way known to a person skilled in the art. For this purpose, the receivers may forward the received signals to an evaluation outside the patient body, e.g. through a wired connection.

In one embodiment of the system, the information about the position and/or orientation of the instrument 3 as determined by means of the tracking arrangement 2 is used to display a representation of the instrument 3 in one or more x-ray image(s). In this embodiment, the system comprises a registration unit 9, which obtains the one or more images from the x-ray device 1 and receives information about the position and/or orientation of the instrument 3 from the tracking arrangement 2. On the basis of the information about the position and/or orientation of the instrument 3, the registration unit 9 determines a position and/or orientation of a model of the instrument 3 in the x-ray image frame and positions the representation of the instrument 3 in the one or more stored x-ray image(s) in accordance with the determined position and/or orientation of the model.

The registration unit 9 may be configured as a data processing device, such as a computer, which particularly has interfaces for receiving x-ray images from the x-ray device 1, for receiving the information about the position and/or orientation of the instrument 3 from the tracking arrangement 2 and for outputting x-ray images overlaid with the representation of the instrument 3 to the display unit 8. Further, the registration unit 9 comprises a processing unit which is programmed to carry out the procedures and functions for overlaying the x-ray images with the representations of the instrument 3. In case the instrument 3 is an imaging probe, the registration unit 9 may comprise a further interface for receiving images acquired using the imaging probe, and the processing unit is programmed to process these images as will be explained further below.

In order to visualize the representation of the instrument 3 in an x-ray image, the registration unit 9 overlays the x-ray image 20 with the representation of the instrument 3. The representation may be opaque so that those parts of the x-ray image which are covered by the representation cannot be seen. However, it is likewise possible that the representation has a certain level of transparency so that both the representation and the covered part of the x-ray image can be seen. Further, the representation of the instrument 3 may have any form which allows for visualizing the position and/or orientation of the instrument 3 or parts thereof in the x-ray image(s).

Figure 3A:
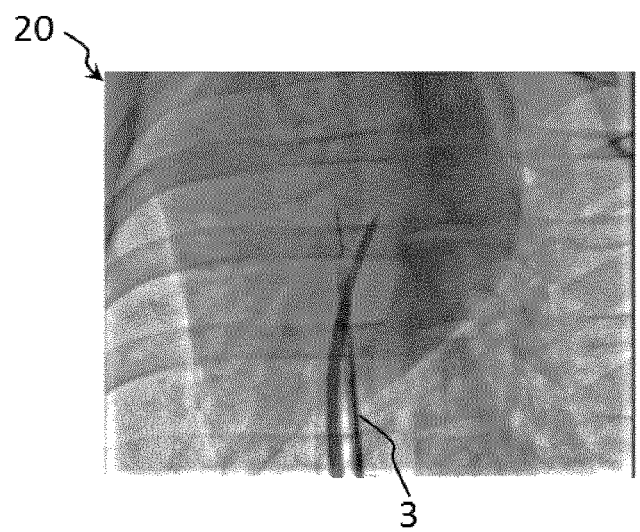
FIGS. 3A-3C show exemplarily embodiments of the visualization according to the invention.
Figure 3B:
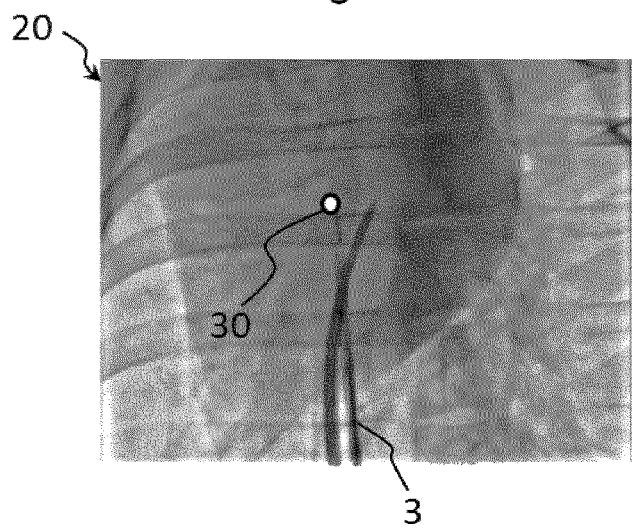
Figure 3C:
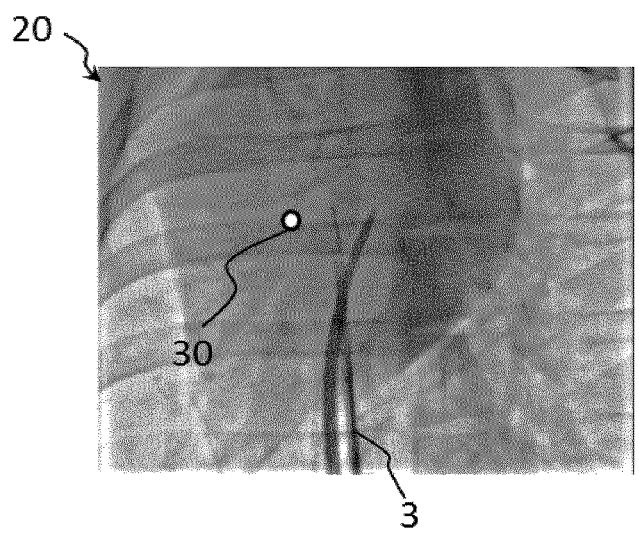

In one implementation, shown in FIGS. 3B and 3C, the representation may be a mark 30, such as a dot, marking the position of certain point of the instrument 3 in the x-ray image(s). This point may particularly be the tip of the instrument 3, since it is usually important in surgical tasks to accurately position the tip of the instrument 3 in the imaged region of interest. In order to arrange the mark in the x-ray image(s), it is only necessary to track the position of the relevant point of the instrument 3 using the tracking arrangement 2. Information about the orientation of the instrument 3 is not required in order to position the mark in the x-ray image(s). In FIG. 3B the position of the distal portion of the instrument 3 is represented by a mark 30 when the positions and/or orientations from the tracking frame are transformed into the extracorporeal image frame. In a further step, illustrated in FIG. 3C, the x-ray image is preserved and the position of the projection of the instrument on the x-ray image is unchanged, however a change in position of the instrument during a clinical procedure is visualized by a displacement of the mark 30 representing an actualized position of the distal tip of the instrument 3. As a result, a real-time position of a portion of the instrument 3 that is tracked by the tracking arrangement 2 is overlaid over an x-ray image 20 acquired in the past. This represents an important advantage in reducing x-ray dose to patient and physician since the physician does not need a confirmation of the position of the instrument by actualizing the x-ray image comprising the projection of the instrument.

In further implementations, the representation of the instrument 3 may be derived from an expanded graphical model of the instrument 3. Such a model may correspond to a line representing the connection between two specific points of the instruments 3, where one of these points preferably again corresponds to the tip of the instrument 3. In case the instruments 3 branches into several section—which may provide plural tips of the instrument 3, for example—the model may also comprise several lines, e.g.

one line for each section. In further embodiments, more realistic three-dimensional models may be used, such as, for example, a model substantially having the actual shape of the instrument 3. Such a model may be configured as a wireframe model or a polygon mesh, for example.

The x-ray image frame corresponds to a three-dimensional coordinate system which is arranged at a certain fixed position and in a certain fixed orientation with respect to the radiation detector 4. This particularly means the original of the x-ray image frame is arranged at a defined location with respect to the radiation detector 4 and that the coordinate axes have a defined orientation with respect to the radiation detector 4. Thus, each pixel of the x-ray images or equivalently each detector element of the radiation detector 4 corresponds to fixed position (i.e. fixed x, y and z coordinates) in the x-ray image frame. For instance, the x-ray image frame may be defined such that its x-y plane corresponds to the surface of the radiation detector 4. However, other choices are likewise possible.

The tracking arrangement 2 determines the position and/or orientation with respect to its own three-dimensional tracking frame. During one session (i.e. one uninterrupted use for a particularly patient), the tracking frame is in principle arranged in fixed position and orientation relative to the x-ray image frame. In some implementations of the tracking arrangement 2, such as implementations using electromagnetic tracking or optical shape sensing, this can be achieved by keeping the components outside the patient body at the same place during a session, for example. However, the relative position and/or orientation of the tracking frame with respect to the x-ray image frame may change between sessions. Such changes may result from changes of the position and/or orientation of the components of the tracking arrangement 2 outside the patient body and/or from changes of the position of the radiation detector 4, e.g. due to movements of the gantry.

Moreover, the measurement signals acquired by the tracking arrangement 2 may comprise systematic errors. Such errors may effectively be regarded as an unknown displacement and/or rotation of the tracking frame. For instance, such errors occur in electromagnetic tracking in case metal is present in the tracking region.

Figure 5A:
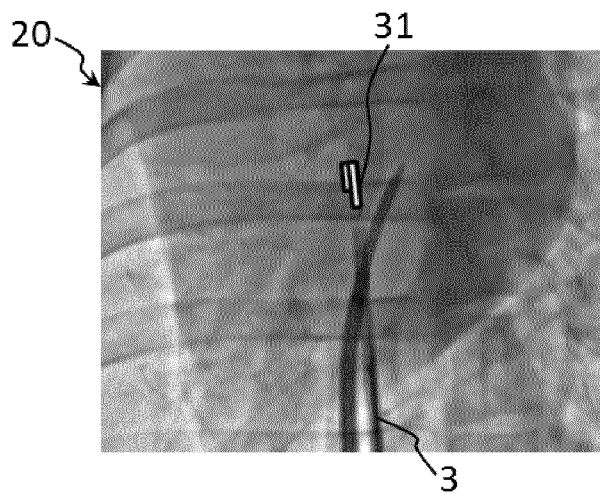
FIGS. 5A-5C show embodiments of the visualization according to the invention, comprising the projection of the graphical model of the instrument.
Figure 5B:
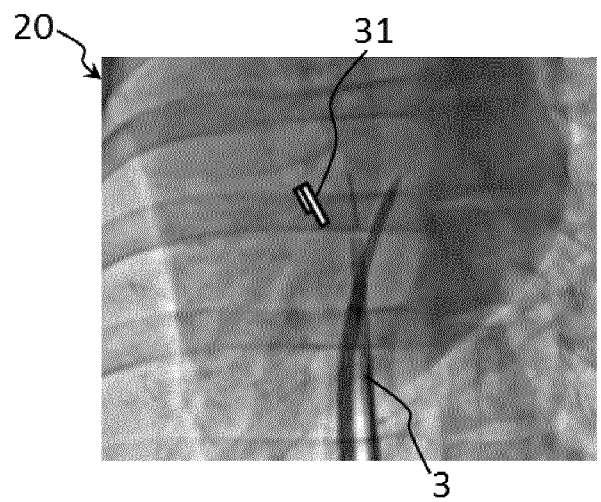

When the position and/or orientation of the instrument 3 is tracked using the tracking arrangement 2, the registration unit 9 visualizes the representation of the instrument 3 in an x-ray image in such a way that the representation substantially has the same position as a projection of the instrument 3 imaged by the radiation detector 4 would have. For this purpose, the registration unit 9 may determine the position and/or orientation of the model of the instrument 3 in the x-ray image frame on the basis of the position and/or orientation of the instrument 3 determined in the tracking frame by means of the tracking arrangement 2. Then, the registration unit 9 may determine the projection of the graphical model 31 of the instrument 3 onto the x-ray image plane and visualize this projection in the x-ray image, as shown in FIGS. 5A and 5B.

Further, the registration unit 9 monitors the information about the position and/or orientation of the instrument 3 provided by the tracking arrangement 2. When the registration unit 9 determines that the position and/or orientation of the instrument 3 changes, the registration unit 9 updates the representation in the currently displayed x-ray image accordingly. For this purpose, the registration unit 9 may again carry out the aforementioned steps with respect to the changed position and/or orientation of the instrument 3.

In order to determine the position and/or orientation of the model in the x-ray image frame on the basis of the information about the position and/or orientation of the instrument 3 in the tracking frame, which are provided by the tracking arrangement 2, a transformation is used. In case the x-ray image frame and the tracking frame have a known position and orientation relative to each other, the transformation may be pre-generated on the basis of relative position and orientation of the frames and stored in the registration unit 9. However, as explained above, the relative position of the x-ray image frame and the tracking frame are not known a priori in many cases. In these cases, an initialization procedure is carried out in order to determine the transform. The initialization procedure is performed prior to the monitoring of the position and/or orientation of the instrument 3 by means of the tracking arrangement 2. In this initialization procedure, a position and/or orientation of the instrument 3 in the x-ray image frame is determined once in order to achieve a mapping between the x-ray image frame and the tracking frame. On the basis of this mapping, the representation of the instrument 3 at subsequent positions and/or orientations determined by means of the tracking arrangement 2 is visualized in one or more x-ray image(s).

By means of the initialization procedure it is possible to register the tracking frame with the x-ray image frame without having to know (or determine) the absolute position and orientation of the tracking frame. Moreover, systematic error of the measurement signals of the tracking arrangement 2 can be compensated for. In this regard, the initialization procedure corresponds to a calibration of the tracking arrangement 2.

In the initialization procedure, the instrument 3 may be imaged using the x-ray device 1 to produce at least one x-ray image showing a projection of the instrument 3 onto the x-ray image plane. FIG. 3A shows an example where the position of the distal portion of the instrument 3 is visible on the x-ray image 20 during initialization phase.

Further, a projection of an expanded graphical model of the instrument 3 onto the x-ray image plane may be determined in the x-ray image frame, which matches the projection of the instrument 3. For this purpose, the same graphical model may be used on the basis of which the representation of the instrument 3 in the x-ray image(s) is generated. In FIG. 5A the projection of the graphical model 31 of the instrument 3 is overlaid over the x-ray image 20. The representation of the projection of the graphical model 31 of the instrument 3 in the x-ray image is according to the positions and/or orientations of the distal portion of the instrument from the tracking frame that are transformed into the extracorporeal image frame. It is also possible to use another model. If another model is used for the initialization procedure, this model is exchanged by the model on the basis of which the representation of the instrument 3 is generated upon completion of the initialization procedure.

In the initialization procedure, the initial position and orientation of the model in the x-ray image frame is determined such that a projection of the model onto the x-ray image plane matches the projection of the medical instrument in the acquired x-ray image. The distance between the initial position and the x-ray image plane can be selected by the registration unit 9 in accordance with an arbitrary default value stored in the registration unit 9. In all other respects, the initial position may be determined by calculating projections of the model for different positions of the model and by selecting the position for which the best-matching projection has been calculated. The selection of the different positions may be made automatically by the registration unit 9 or the positions may be specified by an operator of the imaging system. In the latter case, it may particularly be possible for the operator to displace the model within the x-ray image frame parallel to the x-ray image plane and to rotate the model within the x-ray image frame. During the displacement and/or rotation projections of the model onto the x-ray image plane may be calculated and displayed so that the operator can displace and/or rotate the model until the calculated projection matches the projection of the (real) instrument 3 in the x-ray image.

Depending on the shape of the instrument 3, it may not be possible to uniquely determine a position and orientation of the model of the instrument 3 by determining a projection of the model that matches the projection of the instrument 3 in one x-ray image acquired under a single angle. In this case, one or more further x-ray image(s) may be acquired under one or more further angle(s)—i.e. at different positions of the gantry supporting the x-ray detector—and the registration unit 9 additionally determines projections of the model onto the x-ray image planes of these x-ray images. The initial position is selected such that all calculated projections match the projections of the instrument 3 in the different images.

In addition to the determination of the initial position and orientation of the model of the instrument 3 in the x-ray image frame, the position and orientation of the instrument 3 when acquiring the x-ray image(s) used in the initialization phase is determined by means of the tracking arrangement 2 to thereby determine an initial position and orientation of the instrument 3 in the tracking frame.

On the basis of the initial position and orientation of the model in the x-ray image frame and the position and orientation of the instrument 3 in the tracking frame, the registration unit 9 determines a transform for transforming positions and orientations (which may be expressed as position and orientation vectors, for example) from the tracking frame into the x-ray image system. In particular, the transform is determined such that the transformed position and orientation of the instrument 3 corresponds to the position and orientation of the model.

Upon having determined the transformation, the initialization phase may be completed. Thereupon, the x-ray device 1 is no longer used and the position and/or orientation of the instrument 3 is tracked by means of the tracking arrangement 2, and on the basis of the information about the position and/or orientation of the instrument 3 as determined by the tracking arrangement 2, the representation of the instrument 3 is visualized in the one or more x-ray image(s) by the registration unit 9.

Initially, the registration unit 9 updates the position and/or orientation of the model of the instrument 3 when it determines changes of the position and/or orientation of the instrument 3 on the basis of the information provided by the tracking arrangement 2. For this purpose, the registration unit 9 may transform each new position and/or orientation of the instrument 3 in the tracking frame into the x-ray image frame on the basis of the transform determined in the initialization phase. Hereby, the registration unit 9 may determine the updated position of the model of the instrument 3. Then, the registration unit 9 may determine the projection of the model onto the x-ray image plane and visualizes this projection in an x-ray image.

In one embodiment, one still x-ray image may be displayed at the display unit 8 when the position and/or orientation of the instrument 3 is tracked using the tracking arrangement 2 and the representation of the instrument 3 may be visualized in this x-ray image. Here, the x-ray image, which has been used in the initialization phase, may particularly be displayed. In this case, the x-ray device 1 may be switched into a so-called freeze mode upon completion of the initialization phase, in which the last acquired image is displayed until the freeze mode is switched off. Likewise, it is possible to display an x-ray image of the region acquired at another point in time with the same relative position and orientation of the region of interest with respect to the radiation detector 4.

In a further embodiment, motion of the region of interest is taken into consideration and x-ray images are displayed which show different phases of the motion in accordance with the actual occurrence of these phases. These x-ray images are acquired beforehand using the x-ray device 1 and are stored in the system.

In this embodiment, the system is provided with an additional monitoring device 10 that is configured to acquire a measurement signal which allows for identifying the phases of the motion independent of x-ray imaging. In order to identify phases of the heart motion, an electrocardiograph may particularly be used. In order to identify phases of respiratory motion, a respiratory monitor may be used. For instance, such a monitor may evaluate the breathing air flow of the patient or may optically detect and evaluate motion of the patient's chest caused by the patient's breathing. Likewise the motion of the region of interest may be monitored and the phases of the motion may be identified using images of the region of interest acquired by means of another imaging modality, such as for example ultrasound images. In case the instrument 3 includes an ultrasound probe, the motion of the region of interest may particularly be monitored using the ultrasound images acquired by means of this probe.

The x-ray images of the different motion phases are stored in the system in allocation to the phases. This may be achieved in that a value of the signal provided by the monitoring device 10 or another characteristic of the signal, which allows for identifying the respective phase of the motion, is assigned to each of the stored images. When the position and/or orientation of the instrument 3 is monitored using the tracking arrangement 2, the registration unit 9 evaluates the measurement signal provided by the additional monitoring unit 10 in order to detect the phases of the motion of the region of interest and changes between these phases. For each detected phase, the registration unit 9 controls the system to display the corresponding stored x-ray image, and when a change of the motion phase is detected, the registration unit 9 controls the imaging to replace the currently displayed x-ray image by the stored x-ray image for the newly detected phase. In such a way, moving images of the region of interest are displayed which consist of a series of the stored x-ray images. Further, each displayed x-ray image is overlaid with a representation of the instrument 3 as explained above in order to visualize the current position and/or orientation of the instrument 3.

Figure 2:
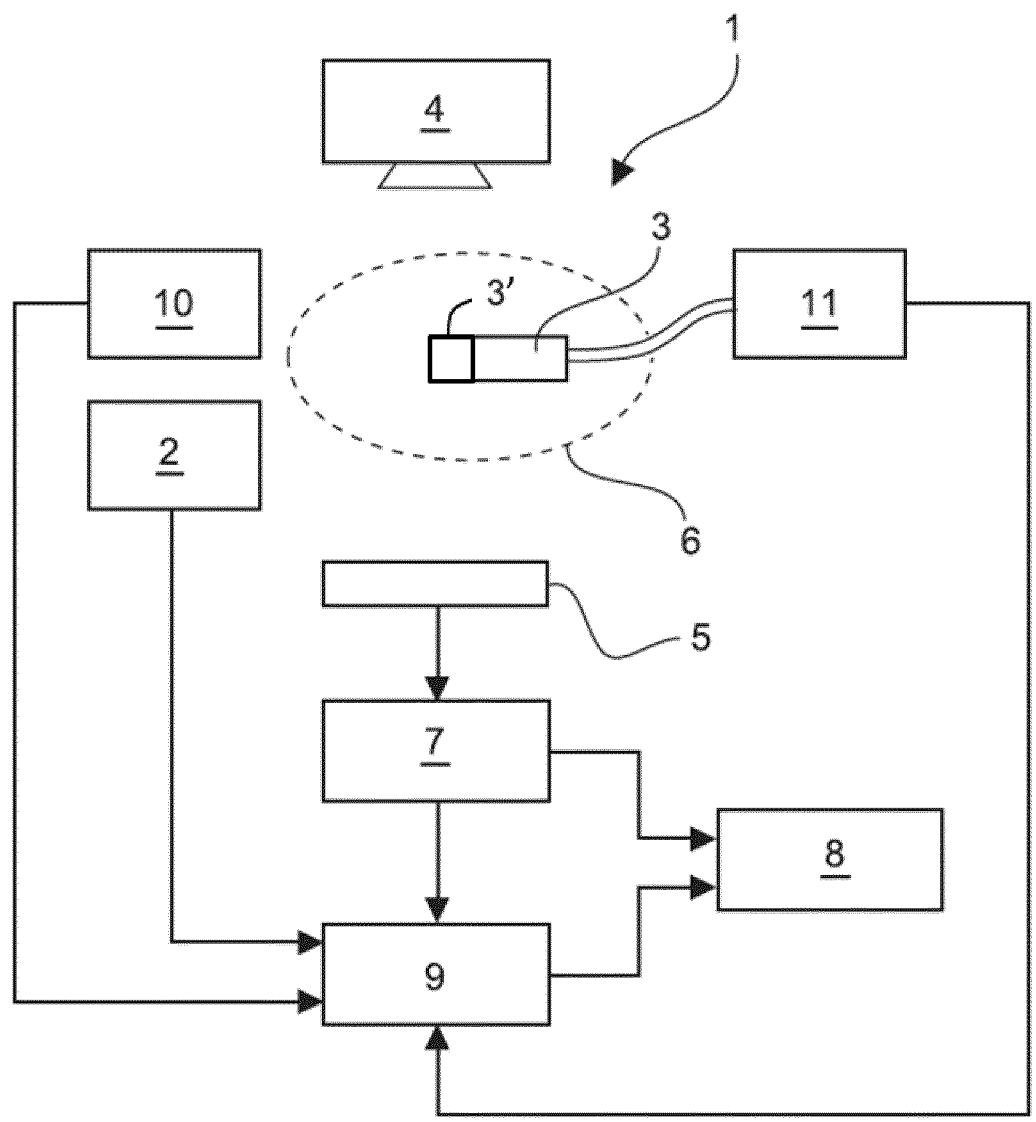
FIG. 2 schematically and exemplarily shows components of a second embodiment of a system according to the invention.

In the aforementioned embodiments, a representation of an instrument 3 is visualized in one or more x-ray image(s) on the basis of information about the position and/or orientation of the instrument 3 determined by means of the tracking arrangement 2. In a further embodiment of the system, which is schematically and exemplarily illustrated in FIG. 2, it is possible to visualize other image objects in the one or more x-ray image(s). In these embodiments, the instrument may particularly be configured as an imaging probe 3' and the image objects may correspond to images acquired using the imaging probe 3'. Such images may be overlaid over the one or more x-ray image(s) in such a way that at least part of the imaged region of interest in the image corresponds to the part of the imaged region of interest shown in the overlaid sections of the x-ray image(s). Such a technique of overlaying images of different imaging modalities is sometimes also referred to as fusion of multi-modal images. The one or more x-ray images may be selected in the same manner as in the embodiments described above.

In one embodiment, the imaging probe 3' may particularly be configured as an ultrasound probe 3'. The ultrasound probe 3' comprises an ultrasound transducer, which produces ultrasound waves and (quasi-) continuously detects ultrasound echoes which are produced when the sound waves are reflected (and/or scattered) by material. In this regard, the ultrasound probe 3' may be configured as intra-cardiac echo (ICE) probe, a transesophageal echo (TEE) probe, an intravascular ultrasound (IVUS) probe, a transthoracic echo (TTE) probe or a vascular probe, for example. The acquired echo signals are processed in an image construction unit 11 in a way known to a person skilled in the art in order to generate moving ultrasound images that can be displayed on the display unit 8 of the system.

In a further embodiment, the imaging probe 3' is configured as an optical coherence tomography (OCT) catheter. Such a catheter comprises an optical fiber for guiding light, particularly near infrared light, to an imaging region and guiding reflected and/or backscattered light back to an image construction unit 11. The image construction unit 11 constructs an image on the basis of the echo time delay of the reflected or backscattered light. In order to determine the echo time delay, the image construction unit 11 may use an interferometer. In this embodiment, light from a light source is split and one part of the light travels to the imaging region and back through the catheter forming one arm of the interferometer and the other part travels through a reference path. The reflected and/or backscattered light from the imaging region is interfered with reflected light from the reference path and detected with a photodetector in order to construct the image.

In a further embodiment, the imaging probe 3' is configured as an endoscope. In this case, the imaging probe 3' comprises an image sensor, particularly a digital image sensor, for (quasi-) continuously acquiring (visual) images. In addition, the imaging probe 3' comprises an illumination unit for illuminating the field of view of the image sensor. The sensor signals are transmitted to an image construction unit 11 connected to the imaging probe 3', and the image construction unit 11 generates visual images on the basis of the sensor signals, which can be displayed by means of the display unit 8.

The imaging probe 3' acquires images of objects within a field of view that has a known fixed arrangement relative to the imaging probe 3'. Therefore, it is possible to determine the position and orientation of the field of view of the imaging probe 3' or the image acquired therewith in the x-ray image frame on the basis of the position and orientation of the imaging probe 3' in the x-ray image frame.

In order to overlay an image acquired by the imaging probe 3' over an x-ray image, the reconstruction unit 9 firstly determines the position and orientation of the imaging probe 3' in the x-ray image frame. This is done by transforming the position and orientation of the imaging probe 3' as determined by means of the tracking arrangement 2 from the tracking frame into the x-ray image frame using the transform described above. On the basis of the position and orientation of the imaging probe 3' in the x-ray image frame and the known position and orientation of the field of view of the imaging probe 3' with respect to the imaging probe 3', the registration unit 9 then determines the position and orientation of the field of view of the imaging probe 3' and image acquired therewith in the x-ray image frame. Thereupon, the registration unit 9 arranges the image acquired by the imaging probe 3' relative to the x-ray image in accordance with the determined position and orientation of the image in the x-ray image frame in order to fuse the image acquired by the imaging probe 3' and the x-ray image.

Figure 4A:
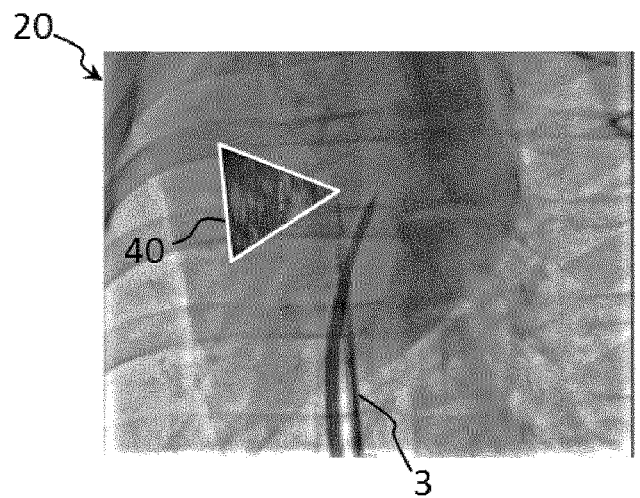
FIGS. 4A-4C show exemplarily further embodiments of the visualization according to the invention, comprising intracorporeal ultrasound image acquired by the instrument.
Figure 4B:
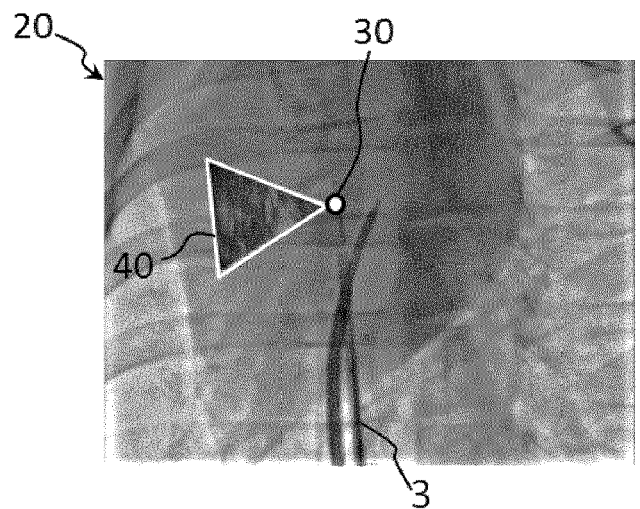
Figure 4C:
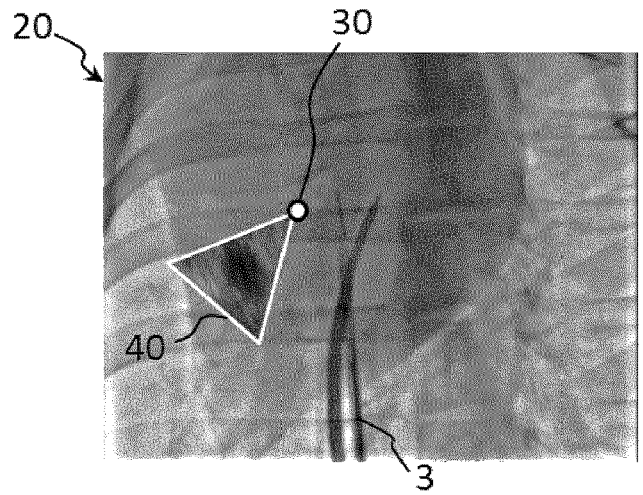
Figure 5C:
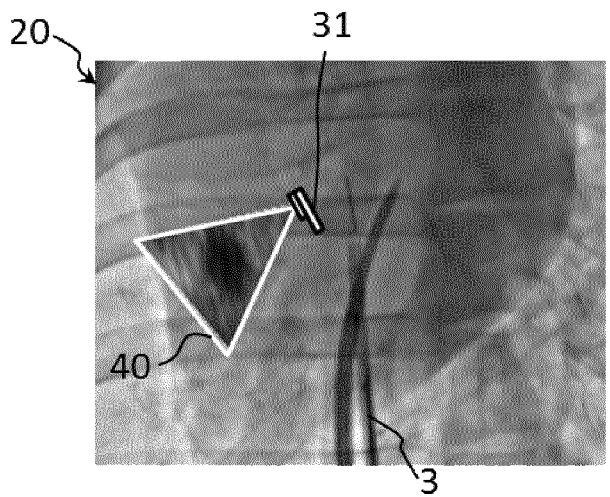

FIGS. 4A-4C correspond to FIGS. 3A-3C, with the addition that instrument 3 comprises an image probe 3' that is configured to receive an intracorporeal image 40, which in the example is an ultrasound image and wherein the image object overlaid over the x-ray image 20 comprises the ultrasound image. FIG. 4C shows that the ultrasound image is arranged relative to the extracorporeal image 20 in accordance with the position and/or orientation of the imaging probe 3' in the extracorporeal image frame 20, therefore the physician is able to intuitively find anatomical structures with the intracorporeal ultrasound imaging probe, without needing to actualize the x-ray image for confirming the position and orientation of the ultrasound probe. FIG. 5C shows a visualization embodiment that further enhances the intuitive interpretation of the localized high resolution intracorporeal images in the context of a larger region of interest imaged from outside of the body, without the physician needing to acquire extracorporeal images repetitively. The position and orientation of the graphical model 31 of the instrument 3 is in accordance with the intracorporeal ultrasound image 40 overlaid over the extracorporeal x-ray image 20. In an embodiment, the intracorporeal image can be actively overlaid over the extracorporeal image like shown in FIG. 5C and it can be deactivated like shown in FIG. 5B.

In the way described above, the registration unit 9 may overlay images which are (quasi-) continuously provided by the imaging probe over the one or more x-ray images.

In all relevant embodiments the registration unit 9 may be comprised in an apparatus standalone or combined with other units configured to carry out various functionalities.

As it already has been revealed at the beginning of the description, other extracorporeal image acquisition systems can be used for providing the extracorporeal image of the region of interest of the body, in order to practice the invention based on the disclosure. Acquiring continuous extracorporeal ultrasound images with an extracorporeal ultrasound imaging system is very challenging due to breathing and heart motion, and it is therefore difficult to continuously track the position and orientation of the instrument. The advantage of the invention is that once a high quality extracorporeal ultrasound image is acquired, there is no further need to use the extracorporeal ultrasound system, since the navigation of the instrument within the region of interest can intuitively be guided based on the visualization of the actual position and/or orientation of the instrument on that particular extracorporeal ultrasound image. Alternatively, when a magnetic resonance imaging system is used for providing extracorporeal images of the region of interest in the body, the major drawback is that acquiring the images is time consuming, which is a limitation for use of magnetic resonance imaging systems for minimally invasive diagnostic and treatment procedures. The invention provides the advantage that the physician is able to navigate the instrument within the region of interest of the body of the patient by using an initial sequence of magnetic resonance images, representing the anatomical structures within the volume comprising the region of interest.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for visualizing an image object relating to an instrument in an extracorporeal image, wherein the apparatus is configured to:
   receive at least one extracorporeal image of a region of interest comprising a projection of the instrument onto an imaging plane with respect to an extracorporeal image frame from an extracorporeal image acquisition system;
   determine at least one of a position and orientation of the instrument in the extracorporeal image frame by matching a projection of a graphical model of the instrument onto the imaging plane to the projection of the instrument onto the imaging plane;
   receive temporal information on at least one of positions and orientations of the instrument in the region of interest with respect to a tracking frame from a tracking arrangement;
   register the at least one of the position and orientation of the instrument in the extracorporeal image frame to the at least one of the position and orientation of the instrument in the region of interest with respect to a tracking frame in an initial instance;
   transform the at least one of the positions and orientations of the instrument from the tracking frame at any later instance into the extracorporeal image frame using a transform;
   output a visualization of the image object in the at least one extracorporeal image based on the transform, wherein the image object relates to at least one of a position and an orientation of the instrument at a later instance than when the at least one extracorporeal image is acquired,
   wherein the projection of the graphical model of the instrument onto the imaging plane is according to at least one of the positions and orientations of a distal portion of the instrument from the tracking frame that are transformed into the extracorporeal image frame.

2. The apparatus according to claim 1, wherein the apparatus is further configured to:
   receive an intracorporeal image from an imaging probe of the instrument, and wherein the image object corresponds to the intracorporeal image acquired using the imaging probe.

3. The apparatus according to claim 1, wherein the visualization comprises overlaying the image object over the extracorporeal image.

4. The apparatus according to claim 2, wherein the apparatus is configured to arrange the image object relative to the extracorporeal image in accordance with the at least one of the position and orientation of the imaging probe in the extracorporeal image frame.

5. The apparatus according to claim 2, wherein the intracorporeal image is one of an ultrasound image and an optical coherence tomography image.

6. The apparatus according to claim 1, wherein the image object comprises a representation of the instrument.

7. The apparatus according to claim 6, wherein representation of the instrument comprises a mark representing one of a predetermined point of the instrument, a projection of a model of the instrument and the graphical model of the instrument.

8. A system comprising:
   the apparatus according to claim 1,
   the extracorporeal image acquisition system,
   the tracking arrangement, and
   the instrument.

9. The system according to claim 8, wherein the extracorporeal image acquisition system is based on x-ray.

10. The system according to claim 8,
    wherein the instrument comprises an imaging probe for providing intracorporeal image,
    wherein the apparatus is configured to receive the intracorporeal image from the imaging probe of the instrument, and
    wherein the visualization of the image object corresponds to the intracorporeal image in the at least one extracorporeal image.

11. The system according to claim 10, wherein the apparatus is configured to arrange the image object relative to the extracorporeal image) in accordance with the at least one of the position and orientation of the imaging probe in the extracorporeal image frame.

12. The system as defined in claim 9, wherein the extracorporeal image is selected from a plurality of stored x-ray images of the region of interest acquired for different phases of a motion of the region of interest, the selected image being acquired for a phase of the motion of the region of interest occurring when the at least one of the position and orientation of the instrument is determined using the tracking arrangement.

13. The system as defined in claim 12, further comprising a monitoring device configured to acquire at least one measurement signal indicative of the phase of the motion of the region of interest, wherein the apparatus is configured to identify the phase of the motion of the region of interest occurring when the changed at least one of position and orientation of the instrument is determined on the basis of the measurement signal.

14. A method of visualizing an image object relating to an instrument in an extracorporeal image comprising:
    receiving at least one extracorporeal image of a region of interest comprising a projection of the instrument onto an imaging plane with respect to an extracorporeal image frame;
    determining at least one of a position and orientation of the instrument in the extracorporeal image frame by matching a projection of a graphical model of the instrument onto the imaging plane to the projection of the instrument onto the imaging plane;
    receiving temporal information on at least one of positions and orientations of the instrument in the region of interest with respect to a tracking frame;
    registering the at least one of the position and orientation of the instrument in the extracorporeal image frame to the at least one of the position and orientation of the instrument in the region of interest with respect to a tracking frame in an initial instance;
    transforming the at least one of the positions and orientations of the instrument from the tracking frame at any later instance into the extracorporeal image frame by using a transform; and outputting a visualization of the image object in the at least one extracorporeal image based on the transform, wherein the image object relates to at least one of a position and an orientation of the instrument at a later instance than when the at least one extracorporeal image is acquired, wherein the projection of the graphical model of the instrument onto the imaging plane is according to the at least one of positions and orientations of a distal portion of the instrument from the tracking frame that are transformed into the extracorporeal image frame.

15. A non-transitory computer-readable medium having stored therein a computer-executable program comprising program code for causing a computer to carry out the method of visualizing an image object relating to an instrument in an extracorporeal image as claimed in claim 14, when run on the computer.

16. The method of claim 14, further comprising receiving an intracorporeal image from an imaging probe of the instrument, wherein the image object corresponds to the intracorporeal image acquired using the imaging probe.

17. The method of claim 16, further comprising arranging the image object relative to the extracorporeal image in accordance with the at least one of the position and orientation of the imaging probe in the extracorporeal image frame.

18. The method of claim 16, wherein the intracorporeal image is one of an ultrasound image and an optical coherence tomography image.

19. The method of claim 14, wherein the visualization comprises overlaying the image object over the extracorporeal image.

20. The method of claim 14, wherein the extracorporeal image is an x-ray image.

* * * * *